United States Patent [19]
Russo

[11] 4,120,299
[45] Oct. 17, 1978

[54] SNORE-PREVENTION ARTICLE AND PROCESS FOR MANUFACTURING THE SAME

[76] Inventor: Joseph J. Russo, 6240 B Tapia Dr., Malibu, Calif. 90265

[21] Appl. No.: 753,399

[22] Filed: Dec. 22, 1976

Related U.S. Application Data

[63] Continuation-in-part of Ser. No. 679,526, Apr. 23, 1976, abandoned.

[51] Int. Cl.² .............................................. A62B 7/10
[52] U.S. Cl. .............................................. 128/140 N
[58] Field of Search ........... 128/140 N, 140 R, 132 R, 128/151, 269; 55/DIG. 35; D33/32 R, 32 F; D11/119

[56] References Cited

U.S. PATENT DOCUMENTS

| | | | |
|---|---|---|---|
| 1,474,710 | 11/1923 | Grier | 55/DIG. 35 |
| 1,997,467 | 4/1935 | Manley | 128/269 |
| 1,997,467 | 4/1935 | Manley | 128/269 X |
| 3,095,877 | 7/1963 | Rowan | 128/296 |
| 3,424,152 | 1/1969 | Kuhlman | 128/132 R |
| 3,464,413 | 9/1969 | Goldfarb et al. | 128/269 X |

*Primary Examiner*—Henry J. Recla
*Attorney, Agent, or Firm*—Warren T. Jessup

[57] ABSTRACT

A snore-prevention article is provided which is intended to be worn in a person's nose while the wearer sleeps, and which serves to prevent snoring by creating a laminar rather than a turbulent air flow through the nose. The article is formed of a piece of cotton batting, or similar material, having a dumbbell configuration with a ball at each end and an elongated flexible thin interconnecting central portion integral with the balls. The invention is also concerned with a simple process for manufacturing the article.

6 Claims, 6 Drawing Figures

SNORE-PREVENTION ARTICLE AND PROCESS FOR MANUFACTURING THE SAME

BACKGROUND OF THE INVENTION

The human palate consists of two portions, the hard palate and the soft palate. The hard palate underlies the nasal cavity, whereas the soft palate hangs like a curtain between the mouth and the nasal pharynx. The soft palate is a backward continuation of the hard palate. The free margin of the soft palate connects on each side with two folds of mucous membrane. In the mid-line the margin extends into a finger-like projection known as the uvula.

Snoring is produced by vibration of the uvula, the vibration being caused by turbulence in the air drawn in through the nose of the sleeper. The article of the present invention is adapted to be inserted into the nose in a position in which it does not interfere in any way with normal breathing, but which creates a laminar rather than a turbulent air flow through the nose of the sleeper to prevent vibration of the uvula, and thereby to prevent snoring.

The article of the invention is light in weight, and it can be worn comfortably without the wearer even being aware of its presence. Moreover, the article may be produced and sold at minimal cost to be readily disposable after each use.

DETAILED DESCRIPTION OF THE ILLUSTRATED EMBODIMENT

Figure 1:
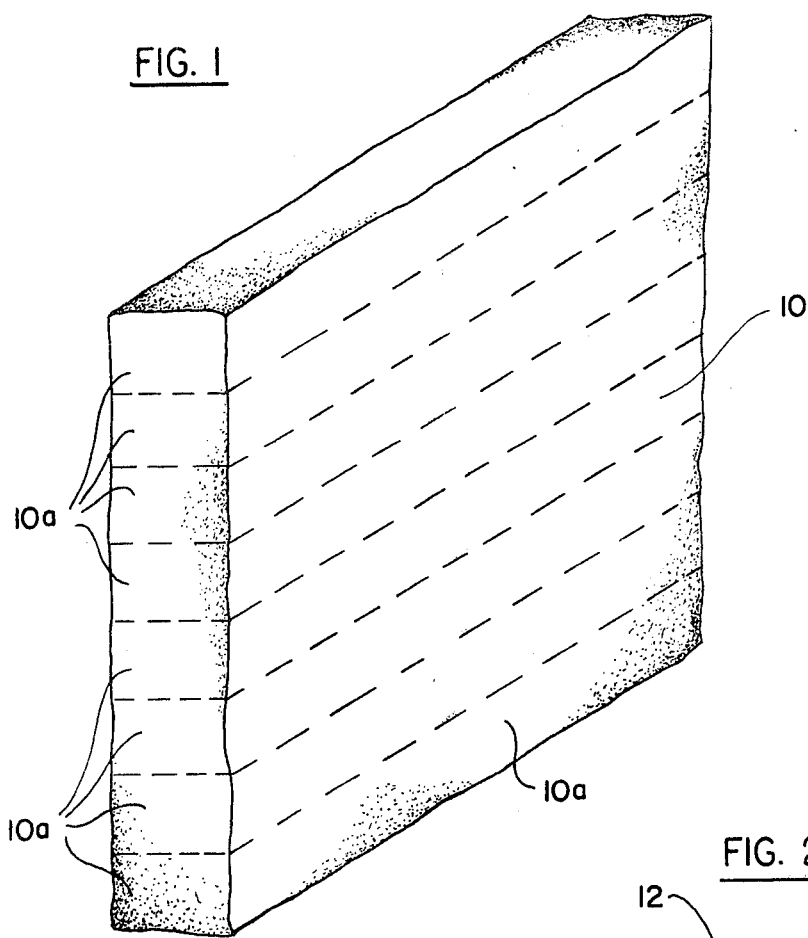
FIG. 1 is a perspective representation of a sheet of cotton batting, from which strips can be cut and formed into the article of the invention.

In the manufacture of the article of the invention, in one of its embodiments, a sheet of cotton batting 10, such as shown in FIG. 1, is cut into a series of strips 10A.

Figure 2:
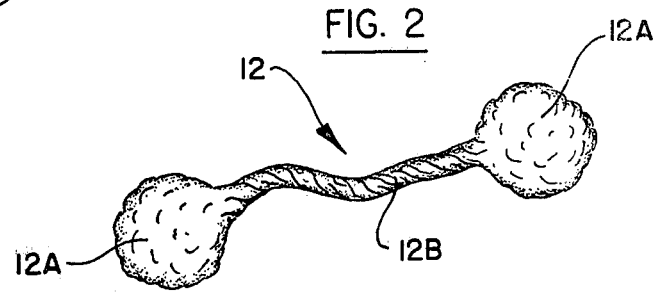
FIG. 2 is a representation of the article in one of its embodiments.

The central portion of each strip is then rolled to a thin flexible elongated section 12B, and the ends of each strip are formed into balls 12A, so as to form the article designated 12 in FIG. 2.

Figure 3:
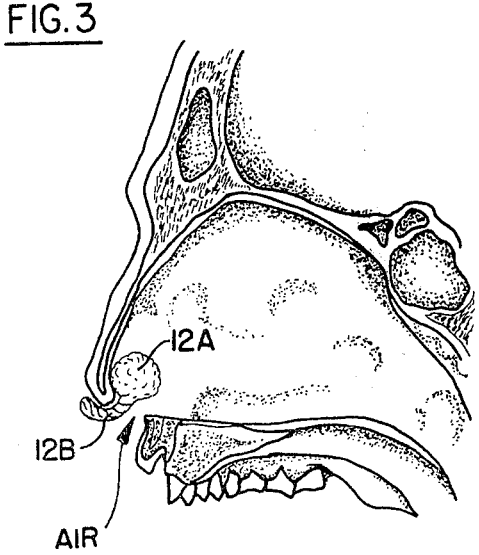
FIG. 3 shows the article in place in the nose of a wearer.

The balls 12A have a shape and size to be fitted into the vestibule of the human nose, as shown in FIG. 3, and the article is held in the illustrated position while the wearer sleeps. As shown in FIG. 3, the article does not interfere in any way with the passage of air through the nose. However, the article does prevent turbulence, so that the air flow is laminar.

As explained above, the laminar air flow through the nose does not have any tendency to vibrate the uvula, so that snoring is prevented.

Figure 4:
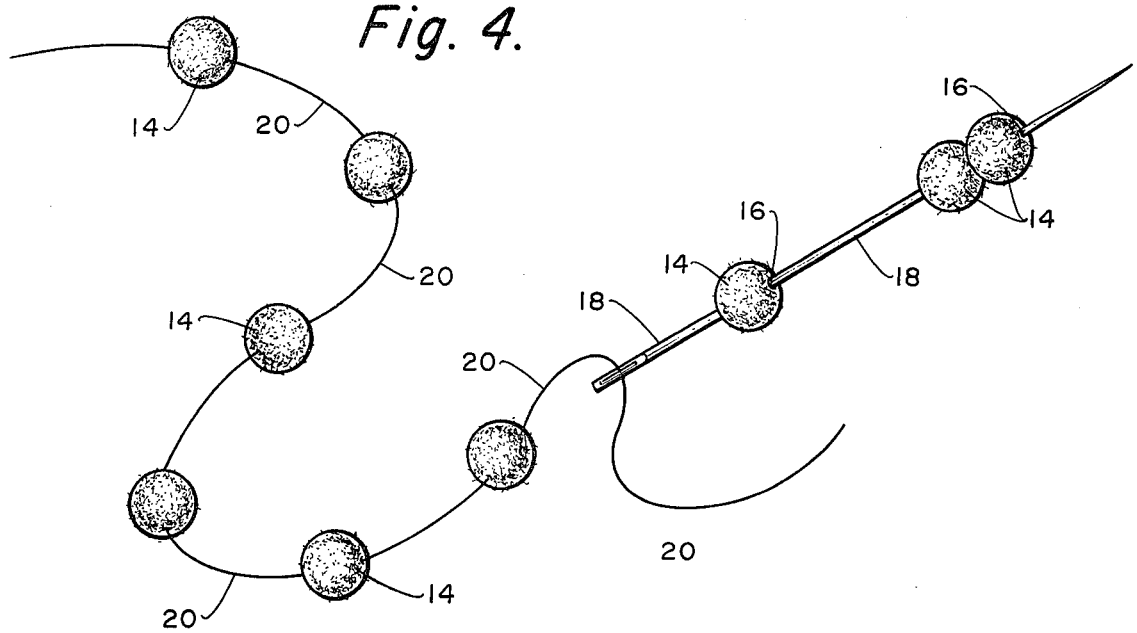
FIGS. 4, 5, and 6 show alternative method of making the device.
Figure 5:
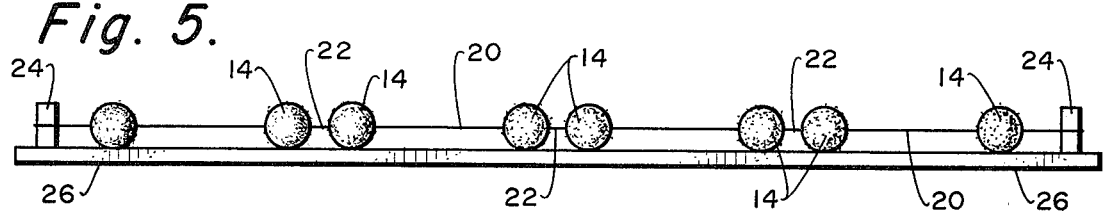
Figure 6:
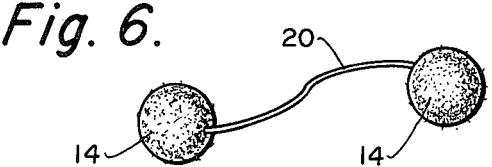

An alternative and somewhat simpler method of making the snore-prevention devices is illustrated in FIGS. 4 through 6. In these figures the cotton balls, instead of being formed integral with the joining strand, as illustrated in FIG. 2, are cotton balls 14 having a hole 16 through their center when they are formed. The cotton balls 14 are then strung on a thin, resilient, non-toxic thread 20 with a needle 18, as illustrated. After threading a number of the cotton balls on the thread 20, the ends of the thread are then tacked down on a board and the cotton balls 14 positioned at alternate long and short intervals, as illustrated in FIG. 5. The cotton balls 14, after proper spacing, are glued to the thread with a non-toxic adhesive, allowed to dry, and then cut at points 22, forming a finished product, as illustrated in FIG. 6. The finished product has the same substantially dumbbell shape but the latter method provides a simpler and more rapid fabrication than the first method.

The cotton balls 14 on the end of the thread 20 are inserted in the vestibule of the nose in the same manner as was shown with the previous embodiment in FIG. 3. Upon awaking, the article may be quickly and easily removed by a slight tug on the thread 20.

The invention provides a simple article of manufacture that may be comfortably worn, and which serves to prevent snoring. The invention also provides a simple and inexpensive method for manufacturing the article, as described above.

It will be appreciated that although a particular embodiment of the invention has been shown and described, modifications may be made. It is intended in the claims to cover the modifications which come within the spirit and scope of the invention.

What is claimed is:

1. A snore-prevention device comprising:

a pair of cotton balls, said cotton balls being of a size and shape to fit into the vestibule of the human nose to block the flow of air through the nostril beneath the tip of the nose, leaving the area of the nostril immediately above the lip substantially open, an elongate thread joining said cotton balls to form a dumbbell-like configuration, said elongate thread having a length slightly longer than the distance between the vestibules of the human nose whereby said thread prevents the cotton balls from being drawn into the nose and permits easy removal, and non-toxic securing means for securing said cotton balls to said elongate thread whereby said balls and said thread form a dumbbell-like configuration.

2. The device according to claim 1 wherein said cotton balls have a hole through their center, and said elongate flexible thread passes through said holes and is firmly secured.

3. The device according to claim 2 wherein said securing means is a non-toxic adhesive securing said elongate thread to said cotton balls.

4. A method of preventing snoring comprising:

forming a soft material such as cotton batting or the like into a substantially ball shape, attaching an elongate thread-like material to each ball whereby said balls may be easily removed from the nose after use by a gentle pull on said thread-like material, inserting said ball-like shape material into the vestibule of the nose to block the flow of air through the nostril beneath the tip of the nose, leaving the area of the nostril immediately above the lip substantially open, whereby air is caused to flow into the nose preventing turbulence and thence eliminating snoring effects.

5. The method according to claim 4 including:

connecting said thread-like material together and to both balls whereby a gentle pull on said thread-like material dislodges both balls simultaneously and said thread-like material prevents said balls from being accidentally drawn into the nose if dislodged during sleep.

6. The method according to claim 5 including the steps of:
forming said cotton balls with small holes therein, threading an elongate piece of thread-like material into the holes of each of said balls, securing said balls to said thread with a non-toxic securing means.

* * * * *